(12) United States Patent
Butts

(10) Patent No.: US 6,518,059 B1
(45) Date of Patent: Feb. 11, 2003

(54) HIGH EFFICIENCY MICROPLATE INCUBATOR

(75) Inventor: Charles G. Butts, Weaverville, NC (US)

(73) Assignee: Kendro Laboratory Products, Inc., Ashville, NC (US)

( * ) Notice: Subject to any disclaimer, the term of this patent is extended or adjusted under 35 U.S.C. 154(b) by 63 days.

(21) Appl. No.: 09/686,406

(22) Filed: Oct. 11, 2000

(51) Int. Cl.[7] .............................. C12M 1/02; C12M 1/38
(52) U.S. Cl. ..................... 435/303.1; 435/809; 422/99; 422/104; 219/386; 219/394; 219/428
(58) Field of Search ............................. 435/303.1, 809; 422/104, 99; 219/385, 386, 394, 428, 438, 441

(56) References Cited

U.S. PATENT DOCUMENTS

| | | | | |
|---|---|---|---|---|
| 4,923,816 A | * | 5/1990 | Heeg et al. ................. | 219/401 |
| 5,149,654 A | * | 9/1992 | Gross et al. ................. | 236/3 |
| 5,459,300 A | * | 10/1995 | Kasman ....................... | 219/433 |
| 5,681,492 A | * | 10/1997 | Van Praet .................... | 219/386 |
| 6,262,394 B1 | * | 7/2001 | Shei et al. ................... | 219/385 |

FOREIGN PATENT DOCUMENTS

JP 8-271391 A * 10/1996

* cited by examiner

*Primary Examiner*—William H. Beisner
(74) *Attorney, Agent, or Firm*—Baker & Hostetler L.L.P.

(57) ABSTRACT

A laboratory microplate incubator (10) including a housing (12) having a specially-sized, enclosed incubation chamber (24) therein and a temperature control assembly (14) that uniformly maintains the temperature within the incubator in a desired range. The temperature control assembly includes a heater (34) positioned within the housing for heating the chamber, a temperature sensor (38) and a controller (36). Multiple incubation chambers can be electrically controlled by the temperature control assembly in a master incubator. Multiple incubation chambers can be stacked to conserve laboratory space. An externally fillable water reservoir is provided inside the chamber.

21 Claims, 1 Drawing Sheet

HIGH EFFICIENCY MICROPLATE INCUBATOR

BACKGROUND OF THE INVENTION

1. Field of the Invention

The present invention relates to laboratory incubators, and more particularly, to a very small, inexpensive incubator having improved temperature stability, uniformity and temperature recovery response.

2. Description of the Prior Art

The temperature within a laboratory incubator must be maintained within a certain operating temperature range for specimen treatment and evaluation. Therefore, it is common to provide laboratory incubators with heating devices that are periodically cycled to maintain the interior temperature of the incubators in this range. Temperature control must be very precise, with less than 0.5° C. variation desired in order to provide accurate, repeatable results.

Such stable temperature control is difficult to obtain with prior art incubators because they are typically large and hold numerous specimens. This presents a problem because the internal temperature of a large incubator varies from location to location within the incubator. In large incubators, temperature uniformity is poor, with actual individual sample exposure temperatures varying as much as 0.75° C. between specimens in some incubators. Furthermore, when multiple specimens are placed in a large incubator, all the specimens are exposed to temperature variations each time the incubator is opened for access to any specimen. Further, large incubators are not energy efficient when one, or a small number of specimens must be incubated. And, of course, large incubators consume excessive laboratory space.

Accordingly, there is a need for an improved incubator that overcomes the limitations of the prior art.

SUMMARY OF THE INVENTION

The present invention addresses the above-described problems and provides a distinct advance in the art of microplate incubators. More particularly, the present invention provides an improved incubator that offers superior temperature uniformity and stability with a simple construction that reduces individual unit cost and allows for the efficient use of available space.

The incubator of the present invention broadly includes a housing having an enclosed incubation chamber therein; a heater positioned within the housing for heating the chamber; and a controller for regulating the operation of the heater to maintain the chamber at a desired temperature.

The incubator is optimally sized to hold a single standard microplate sample, providing less than 0.02 cubic feet of internal space. Such constrained size ensures the microplate sample is always in near proximity to the heater. The primary thermal path from the heater to the microplate is conductive and therefore more stable and uniform than the convection thermal path experienced by microplate samples in large incubators. The optimal sizing and conductive heat path also provide for improved temperature control when the chamber is accessed because less cooler ambient air can be admitted into the chamber.

In operation, the controller cycles the heater whenever the internal temperature is lower than the set operating temperature of the incubator, thus maintaining the operating temperature of the incubator within a desired range. The construction of the present invention provides improved temperature uniformity and temperature stability by shortening the thermal path between the heater and the specimen, reducing the distance between the heater and the temperature sensor and facilitating the operators' ability to minimize access. The present invention more consistently and uniformly maintains the contained specimen microplate at the set temperature rather than, as in prior art incubators, allowing specimen microplate temperature to suffer temperature fluctuations based on random position and temperature variations within the incubator.

The incubator is configured to allow multiple incubators to be stacked vertically so as to provide efficient utilization of laboratory space. This allows laboratory personnel to establish multiple temperature controlled environments in a compact space.

The incubator also preferably includes an internal water reservoir that can be used to maintain a high humidity environment, reducing evaporation from the microplate sample. The operator can fill or replenish the reservoir externally.

A preferred embodiment of the invention couples a plurality of incubators together wherein secondary microplate incubator units may be electrically linked to a master incubator. The secondary microplate incubator units are simplified and less expensive because the temperature controller and sensor are not required. All units are maintained at the desired temperature based on the controller and sensor in the master incubator. A single control for multiple incubators also simplifies operation.

These and other important aspects of the present invention are described more fully in the detailed description below.

BRIEF DESCRIPTION OF THE DRAWING FIGURES

A preferred embodiment of the present invention is described in detail below with reference to the attached drawing figures, wherein.

Figure 1:
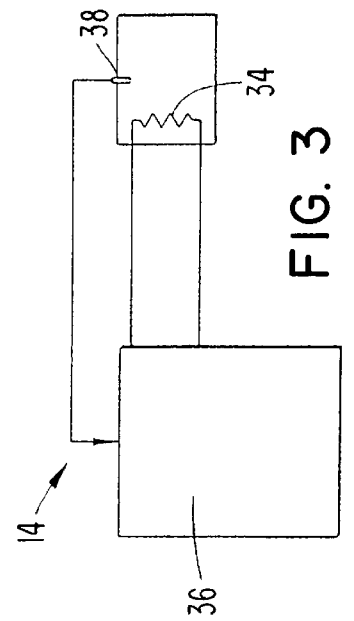
FIG. 1 is a perspective view of a microplate incubator constructed in accordance with a preferred embodiment of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

Referring to the drawing figures, a laboratory incubator 10 constructed in accordance with a preferred embodiment of the invention is illustrated. The incubator includes a housing 12 and a temperature control assembly broadly referred to by the numeral 14.

In more detail, the housing 12 includes spaced-apart outer walls 16, inner walls 18 and a door 20. The outer walls 16, inner walls 18 and door 20 are preferably formed of stainless steel, but may be manufacture from other suitable materials such as aluminum or high temperature plastic as a matter of design choice. The outer walls 16 illustrated in FIG. 1 are specially configured to allow multiple incubators to be safely stacked vertically, while allowing access to each incubator.

More specifically, the inner walls 18 define an incubation chamber 24 therein and include a bottom inner wall 22 which supports a microplate. The chamber 24 is specially sized to hold only one microplate, having an internal volume of less than 0.02 cubic feet. The small volume of the incubator ensures improved temperature uniformity by positioning the microplate a consistent, shortened spacing from the inner walls 18. Thermal insulation 26 is present between the outer walls 16 and the inner walls 18.

As seen in FIG. 1, the door 20 includes an inner door wall 28 and an outer door wall 30. In the preferred embodiment, a water reservoir 32 is provided in the inner door wall 28, which can be filled through the outer door wall 30. Thermal insulation (not shown) is also present between the inner door wall 28 and the outer door wall 30.

Figure 3:
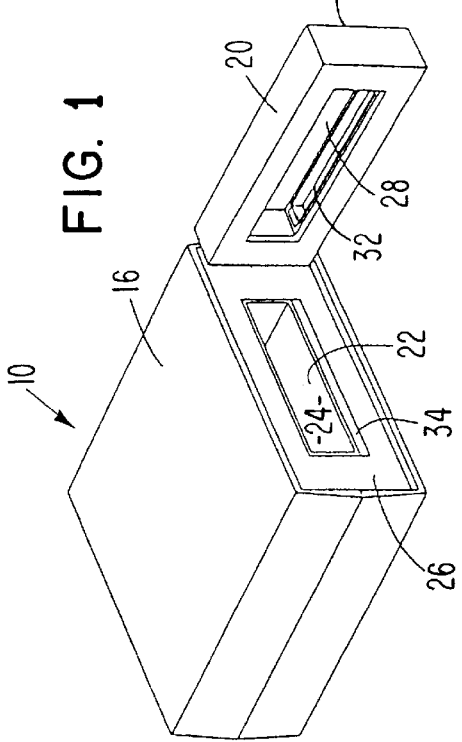
FIG. 3 is a schematic diagram of the temperature control assembly of the incubator in accordance with a preferred embodiment of the present invention.
Figure 4:
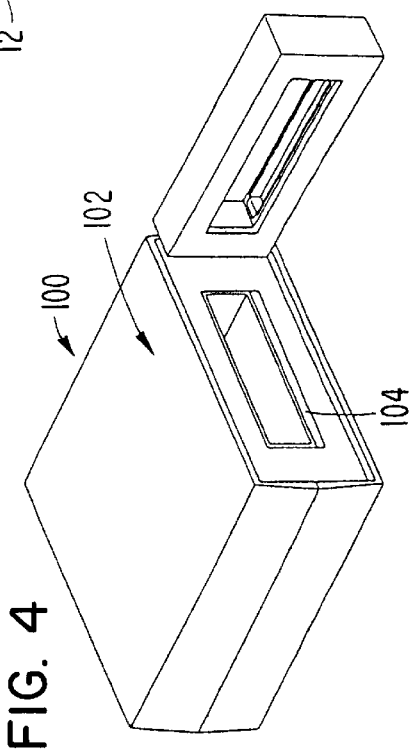
FIG. 4 is a perspective view of a microplate incubator constructed in accordance with an alternative embodiment of the present invention.

The temperature control assembly 14 is operatively coupled with the housing 12 to control the temperature within the chamber 24 so that the temperature remains within a desired range. For example, in one application, the control assembly 14 maintains the temperature within the chamber 24 at approximately 42° C.±0.4° C. As best illustrated in FIG. 3, the temperature control assembly 14 includes a heater 34, a controller 36 and a temperature sensor 38. The proximity of the temperature sensor 38 to the heater 34, in combination with the constrained volume of the chamber 24, enables the temperature control assembly 14 to maintain a uniform temperature within 0.2° C. within the chamber 24.

The heater 34 is positioned between the outer walls 16 and the inner walls 18 of the housing 12 and is operable for heating the incubation chamber 24 when the internal temperature in the incubator 10 is below the incubator's desired operating temperature. The heater 34 may be any conventional heating device, but preferably includes a low watt density, high surface area, contact resistive heater. Thermal insulation 26 is present between the heater 34 and the outer walls 16, but not between the heater 34 and the innerwalls 18. In the preferred embodiment the heater is bonded with the bottom inner wall 22.

The controller 36 directs electrical power from a power supply (not shown) to cycle the heater 34. The controller 36 may be any conventional programmable microprocessor device. The controller 36 allows the operator to adjust thermal conditions in the chamber 24.

Figure 2:
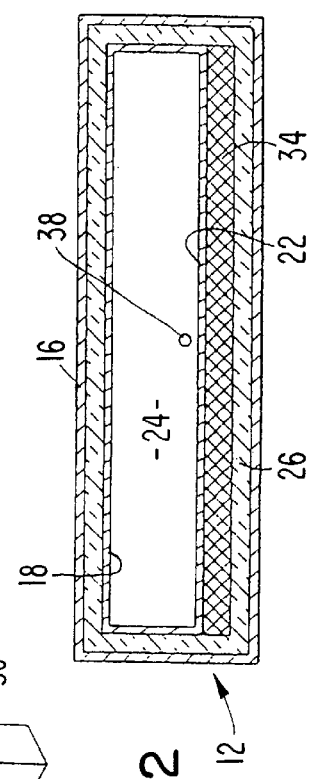
FIG. 2 is a vertical sectional view of a microplate incubator constructed in accordance with a preferred embodiment of the present invention.

As illustrated in FIG. 2, the temperature sensor 38 is mounted within the housing 12 for monitoring the temperature within the incubation chamber 24. More specifically, the temperature sensor 38 is preferably positioned inside the inner walls 18 of the housing 12 so that it monitors the temperature within the incubation chamber 24. Alternatively, the temperature sensor 38 may be in contact with the bottom inner wall 22 so as to detect inner wall temperature. As illustrated in FIG. 3, the temperature sensor 38 is coupled with the controller 36 for delivering signals representative of the sensed temperature thereto.

In operation, an operator preferably establishes the desired temperature of the incubator 10 prior to the insertion of the specimen microplate. The operator adjusts the controller 36 of the temperature control assembly 14 to the required temperature, ensuring that power is available to the assembly 14. The temperature control assembly 14 functions to establish and maintain the temperature within the incubation chamber 24. Specifically, whenever the internal temperature in the chamber 24 is lower than the desired operating temperature of the incubator 10, the controller 36 cycles power to the heater 34 to maintain the operating temperature of the chamber 24 within a desired range.

Due to the limited chamber 24 size, the present invention quickly establishes the required temperature in a uniform pattern. If the specimen requires a saturated water vapor atmosphere, the operator should fill the reservoir and maintain it by filling as necessary. The operator then may place the microplate specimen in the chamber 24. The temperature senor will provide a temperature signal to the controller, which will cycle the heater as necessary to maintain the operator selected temperature.

Figure 5:
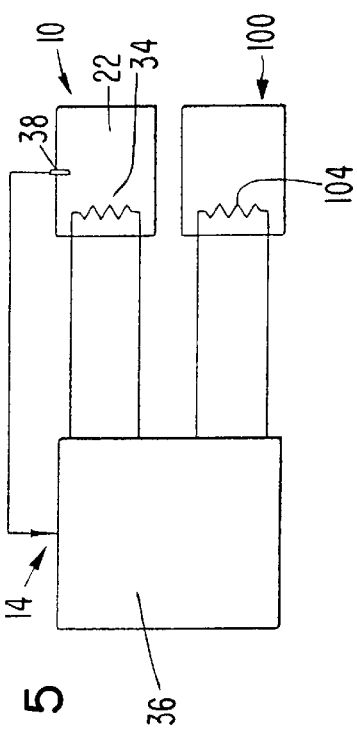
FIG. 5 is a schematic diagram of the temperature control assembly of the incubator in accordance with an alternative embodiment of the present invention.

FIG. 5 illustrates an alternative embodiment, wherein the incubator 100 is identical to the embodiment described above except that it does not include a temperature sensor and temperature controller. The alternative embodiment must be coupled with a master incubator that practices these features.

The incubator 100 broadly includes a housing 102 and a heater 104. In the preferred embodiment, the heater 104 is of the same make and style as the heater in the master incubator. The heater 104 is provided with power in response to the temperature control assembly of the master incubator.

As illustrated in FIG. 5, an operator may electrically link the heaters 104 of a desired number of secondary incubators to the temperature control assembly 14 of a master incubator. The temperature control assembly 14 is then set to establish and maintain the temperature within the master incubator 10 and the secondary incubator 100. The heater 104 maintains the temperature in each secondary incubator at substantially the identical temperature of the master incubator. When a saturated water vapor atmosphere is desired, the operator must fill the reservoir of each incubator.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A laboratory incubator comprising:
   a housing having walls defining an enclosed incubation chamber configured to hold a single standard microplate, said chamber having less than 0.02 cubic feet of internal volume;
   a temperature control assembly including a heater in contact with at least one wall of the incubation chamber, a temperature sensor and a controller coupled to the heater to maintain a uniform temperature within 0.2° C. within the chamber; and
   the housing presenting inner walls, including an inner bottom wall, the housing further presenting outer walls, including an outer bottom wall, and a door presenting an inner door wall and outer door wall, said inner walls and inner door wall together defining the incubation chamber therein,
   wherein an inner wall, including the inner door wall, presenting a water reservoir, the water reservoir capable of being filled through an outer wall, including the outer door wall.

2. A laboratory incubator as in claim 1, the heater being a resistive heaters.

3. A laboratory incubator as in claim 1, the controller including a temperature selector device for operator control of chamber temperature.

4. A laboratory incubator as in claim 1, the temperature sensor being in contact with the walls of the chamber.

5. A laboratory incubator as in claim 1, the housing being configured to allow a plurality of laboratory incubators to be vertically supported thereon.

6. A laboratory incubator as in claim 1, the incubator having thermal insulation between each inner wall and outer wall.

7. A laboratory incubator as in claim 1, the outer walls being constructed from stainless steel.

8. A laboratory incubator as in claim 1, the heater being in contact with the inner bottom wall.

9. A laboratory incubator as in claim 8, the heater being a resistive heater.

10. A laboratory incubator as in claim 9, the resistive heater being a low watt density, high surface contact resistive heater.

11. A laboratory incubator system comprising:
   a first laboratory incubator including a housing having walls defining an enclosed first incubation chamber therein, and a heater in contact with at least one wall of the first incubation chamber;
   a second laboratory incubator including a housing having walls defining an endclosed second incubation chamber therein, and a heater in contact with at least (one wall of the second incubation chamber;
   a temperature control assembly including a controller and a temperature sensor within the first laboratory incubator, wherein the temperature control assembly is coupled to the heaters of both the first and the second laboratory incubators to maintain a uniform temperature within both of the incubation chambers; and
   each housing presenting inner walls, including an inner bottom wall, each housing further presenting outer walls, including an outer bottom wall, and a door presenting an inner door wall and outer door wall, said inner walls and inner door wall together defining the incubation chamber therein,
   wherein an inner wall, including the inner door wall, presenting a water reservoir, the water reservoir capable of being filled through an outer wall, including the outer door wall.

12. A laboratory incubator system as in claim 11, each chamber being configured to hold a single standard microplate, each chamber having less then 0.02 cubic feet of internal volume.

13. A laboratory incubator system as in claim 11, each heater being a resistive heater.

14. A laboratory incubator system as in claim 11, the controller including a temperature selector device.

15. A laboratory incubator system as in claim 11, the temperature sensor being in contact with the walls of the first chamber.

16. A laboratory incubator system as in claim 11, each housing being configured to allow a plurality of laboratory incubators to be vertically supported thereon.

17. A laboratory incubator system as in claim 11, the incubator having thermal insulation between each inner wall and outer wall.

18. A laboratory incubator system as in claim 11, the outer walls being constructed from stainless steel.

19. A laboratory incubator system as in claim 11, the heater being in contact with the inner bottom wall.

20. A laboratory incubator system as in claim 19, the heater being a resistive heater.

21. A laboratory incubator system as in claim 20, the resistive heater being a low watt density, high surface contact resistive heater.

* * * * *

UNITED STATES PATENT AND TRADEMARK OFFICE
CERTIFICATE OF CORRECTION

PATENT NO. : 6,518,059 B1
DATED : February 11, 2003
INVENTOR(S) : Charles G. Butts It is certified that error appears in the above-identified patent and that said Letters Patent is hereby corrected as shown below:

<u>Title page,</u>
Item [73], Assignee, please change "Ashville, NC (US)" to -- Asheville, NC (US) --.

Signed and Sealed this

Fifteenth Day of July, 2003

JAMES E. ROGAN
*Director of the United States Patent and Trademark Office*